(12) United States Patent
Millikin

(10) Patent No.: US 11,877,986 B1
(45) Date of Patent: Jan. 23, 2024

(54) METHOD OF PRECISION DOSING

(71) Applicant: Rory Chesley Patrick Millikin, Kelowna (CA)

(72) Inventor: Rory Chesley Patrick Millikin, Kelowna (CA)

(73) Assignee: Trucelium Inc

( * ) Notice: Subject to any disclaimer, the term of this patent is extended or adjusted under 35 U.S.C. 154(b) by 0 days.

(21) Appl. No.: 18/113,402

(22) Filed: Feb. 23, 2023

Related U.S. Application Data

(63) Continuation-in-part of application No. 17/863,214, filed on Jul. 12, 2022, now abandoned.

(60) Provisional application No. 63/187,909, filed on May 12, 2021.

(51) Int. Cl.
*A61K 36/06* (2006.01)
*A61K 36/185* (2006.01)
*A61K 45/06* (2006.01)

(52) U.S. Cl.
CPC ............ *A61K 36/185* (2013.01); *A61K 36/06* (2013.01); *A61K 45/06* (2013.01)

(58) Field of Classification Search
CPC ...... A61K 36/00; A61K 36/185; A61K 36/06; A61K 2236/00; A61K 2236/30; A61K 2236/50; A61K 36/07; A61K 31/675; A61K 31/4045; A61K 34/06; A23V 2250/208; A23V 2300/14; A23V 2200/31; A23V 2250/2132; A23V 2250/21; G01N 2800/30; G01N 2333/37; A23L 33/105; A23L 2/52; A23L 31/00
See application file for complete search history.

(56) References Cited

U.S. PATENT DOCUMENTS

| | | | |
|---|---|---|---|
| 2018/0221396 A1* | 8/2018 | Chadeayne | A61P 25/00 |
| 2022/0192979 A1* | 6/2022 | Gaya | A61K 9/0095 |
| 2022/0304980 A1* | 9/2022 | Arnold | A61K 9/008 |

* cited by examiner

*Primary Examiner* — Hong T Yoo
(74) *Attorney, Agent, or Firm* — Christopher Pilling

(57) ABSTRACT

Methods of precision dosing matter is provided. The matter, such as plant or fungi matter, include species having or lacking active mind alternating compounds. Various extraction methods are performed to remove these compounds, such that additional compounds of predetermined dosages may be added to the plant or fungi matter until a desired level of compound concentration is reached. Homogenizing and testing is carried out at various points to ensure accurate compound concentration levels.

11 Claims, 4 Drawing Sheets

METHOD OF PRECISION DOSING

CROSS-REFERENCE TO RELATED APPLICATIONS

The present invention is a continuation in part application to utility non-provisional application Ser. No. 17/863,214 filed Jul. 12, 2022 which claims priority to provisional application Ser. No. 63/187,909 filed May 12, 2021, which is hereby incorporated in its entirety at least by reference.

BACKGROUND OF THE INVENTION

1. Field of the Invention

The present invention relates to dosing and more particularly a method of precision dosing matter.

2. Description of Related Art

Psychedelics and *Cannabis* as a health supplement have been practiced for over 1,000 years. It is well known that cannabinoids and psilocybin offer many benefits to users and the following disclosure provides a unique process in effectively providing a desired precision dose of these substances and similar substances.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

It is an object of the present invention to provide precision psilocybin dosing within a fungi. It is a particular object of the present invention to provide precision dosage of compound concentration to plant or fungi matter, wherein the precision dosage includes the full spectrum of compound plant matter, to benefit from the entourage effect. The Entourage Effect is a desired outcome as it is believed to be more powerful than extracted compounds; in essence, the whole is stronger than the (isolated) parts. However, due to the nature of the wide variations in concentration of compounds within natural products, it is desired to ensure that as accurate as possible doses of these compounds are present in the natural plant or fungi matter.

In addition, there often is too strong a concentration of compounds present in the natural product that does not lend well to the desired process known as microdosing. Therefore reducing the concentration of the active compounds like psilocybin or THC is desired. It is also desired to have precision doses of these compounds to ensure that you are not getting too much in your body that may affect your ability to function.

In order to achieve this, a number of key processes can be used. For example, extract as much or all of the compounds as possible from the plant or fungi matter and then add precise doses of the desired compounds back into the matter.

Another method is to simply test the matter beforehand, determine what concentration of the compounds are present, and then add precise amounts of additional compounds to reach a desired level of concentration.

Another embodiment is to cross over the compounds from one species or strain of plant/fungi into the other. For example, adding cannabinoids such as, but not limited to, CBD or THC to a psychedelic mushroom to compliment or add new desired characteristics to the product or vice versa.

In order to do so, a method of precision dosing plant or fungi is provided, comprising steps: (a) providing plant or fungi matter having a compound concentration; (b) extracting at least a portion of the compound concentration from the plant or fungi matter via an extraction method; and, (c) adding additional compounds to reach a desired level of compound concentration within the plant or fungi matter.

In one embodiment, the plant or fungi matter is homogenized after step (a), (b), or (c). In one embodiment, a step of testing the plant or fungi matter to determine the compound concentration is provided. In one embodiment, in step (b), the extraction method is an extraction method selected from a liquid extraction, a chemical extraction, or a mechanical extraction. In one embodiment, in step (a), the plant or fungi matter is in its natural form, a liquid form, a solid form, or powder form. In another embodiment, a step of infusing additional plant or fungi matter not containing a compound concentration with the extracted compounds of step (b) or additional compounds of step (c) is provided.

In another aspect of the invention, a method of precision dosing plant or fungi is provided, comprising steps: (a) providing plant or fungi matter having a compound concentration; (b) testing the plant or fungi matter to determine the compound concentration; and, (c) adding additional compounds to reach a desired level of compound concentration within the plant or fungi matter.

In one embodiment, the plant or fungi matter is homogenized prior to step (b). In one embodiment, the plant or fungi matter is homogenized after step (c). In another embodiment, in step (a), providing additional plant or fungi matter not having a compound concentration. In another embodiment, the plant or fungi matter and the additional plant or fungi matter are homogenized separately or homogenized together to form a blend prior to step (b). In one embodiment, the plant or fungi matter and the additional plant or fungi matter are homogenized together after step (c). In one embodiment, a step of testing the plant or fungi matter to determine the compound concentration after the completion of all steps is provided, then repeating step (c) if necessary.

In yet another aspect of the invention, a method of precision dosing plant or fungi is provided, comprising steps: (a) providing plant or fungi matter having a compound concentration; (b) extracting at least a portion of the compound concentration from the plant or fungi matter via an extraction method; (c) testing the plant or fungi matter to determine the concentration of the compounds remaining; and, (d) adding a predetermined concentration of compounds to the plant or fungi matter to reach a desired level of compound concentration.

In one embodiment, a further step (e) is provided, including testing and analyzing the plant or fungi matter to determine if the desired level of compound concentration was achieved. In one embodiment, a step of testing the plant or fungi matter to determine the compound concentration prior to step (b) is provided. In one embodiment, the plant or fungi matter is homogenized after step (a), (b), or (d). In one embodiment, in step (a), the plant or fungi matter is in its natural form, a liquid form, a solid form, or a powder form. In another embodiment, a step of providing additional plant or fungi matter not having a compound concentration is provided, wherein the additional plant or fungi matter is homogenized with the plant or fungi matter.

The foregoing has outlined rather broadly the more pertinent and important features of the present disclosure so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present disclosure. It should be realized by those skilled in the art that such equivalent structures do not depart from the spirit and scope of the invention as set forth in the appended claims.

BRIEF DESCRIPTION OF THE SEVERAL VIEWS OF THE DRAWINGS

Other features and advantages of the present invention will become apparent when the following detailed description is read in conjunction with the accompanying drawings, in which.

DETAILED DESCRIPTION OF THE PREFERRED EMBODIMENT

The following description is provided to enable any person skilled in the art to make and use the invention and sets forth the best modes contemplated by the inventor of carrying out their invention. Various modifications, however, will remain readily apparent to those skilled in the art, since the general principles of the present invention have been defined herein to specifically provide an improved method for a method of precision dosing plant or fungi.

For the purpose of this disclosure, the word "a" is defined to mean "at least one." The word "*Cannabis*" is defined to mean "any species of the *Cannabis* genus of flowing plants including *Cannabis sativa, Cannabis* indica, *Cannabis ruderalis*, and hemp." The terminology includes the words above specifically mentioned, derivatives thereof, and words of similar import. The word "plant or fungi matter" is defined to mean all mushrooms, *Cannabis*, mycelium, or any other plant or fungi including vegetables, herbs, seeds, nuts, and any other edible plants." The word "compound(s)" is defined to mean any active ingredient including Psychedelics or *Cannabis* which may include any of the following cannabinoids, Psilocin, psilocybin, Lysergic Acid Diethylamide, Baeocystin, N,N-Dimethyltrptamine, Tryptamine, Norbaecystin, Mescaline, Muscimol, Ibotenic Acid, Lysergic Acid, Bufotenin, Beta-Carboline, Ethocybin, indole Alkaloid, 2C-B, O-Acetylpsilocin, Ergine, 25I-NBOMe, Dipropyltrptamine, Diethyltryptamine, 2C-E, 4-Acetoxy-DiPt, Aeruginascin, Salvinorin A, 4-HO-DET, Dilsopropyltryptamine, Glaucine, 4-HO-MET and 4-HO-DiPT, MDMA, Ketamine, Ayahuasca, LSD, and any other compound or chemical known to be a psychedelic or cannabinoid either from natural matter or synthetically designed.

Figure 1:
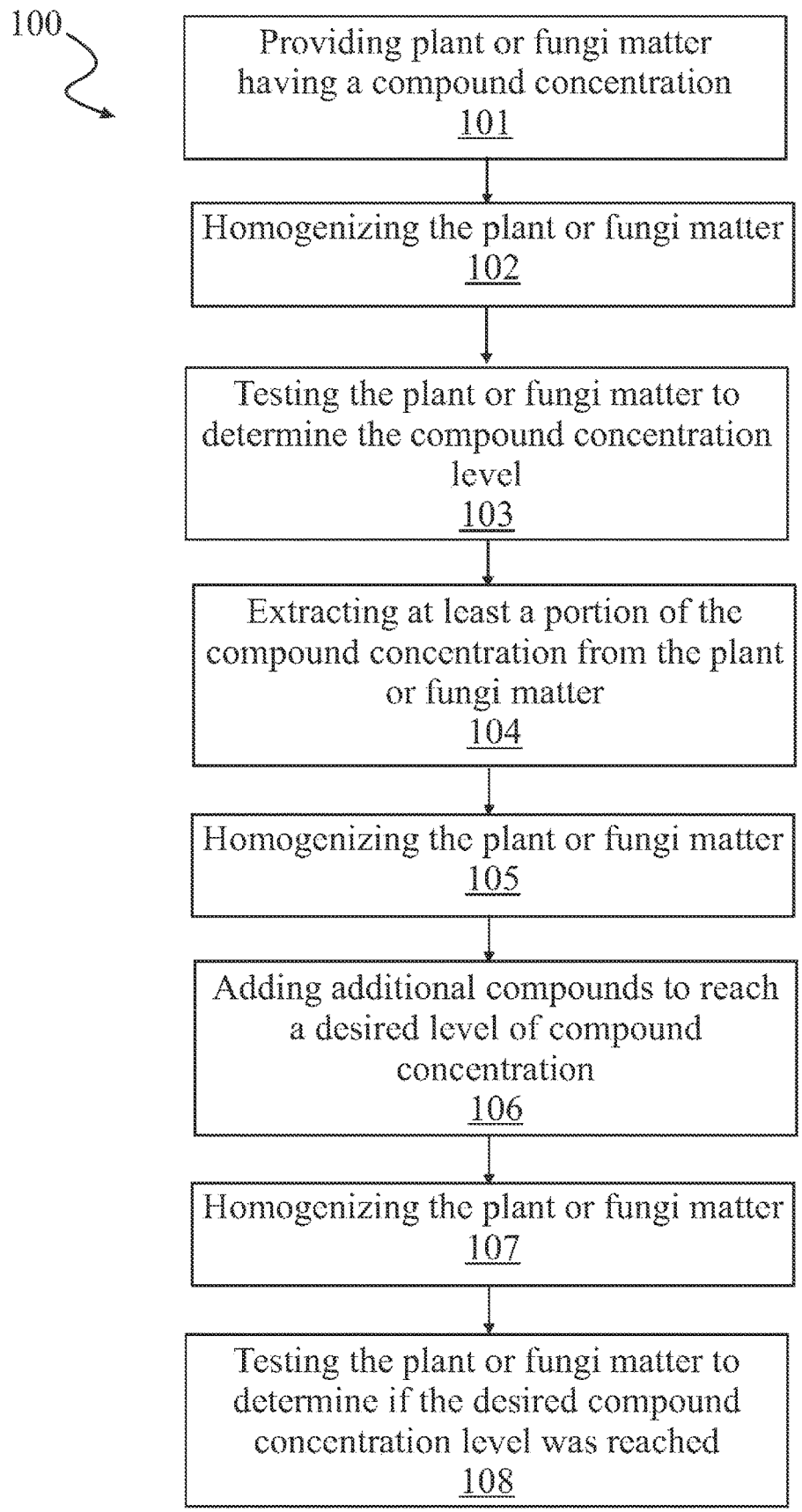
FIG. 1 is a method of precision dosing plant or fungi matter according to an embodiment of the present invention.

FIG. 1 is a method 100 of precision dosing plant or fungi matter according to an embodiment of the present invention. Now referring to FIG. 1, the method 100 is illustrated. First, in step 101, plant or fungi matter having a compound concentration is provided. Referring to the previously defined compound definition, the plant or fungi matter may include any matter, particularly plant or fungi based having a compound concentration, i.e. a detectable level of psychedelics, cannabinoids, drug, stimulants, etc. In one embodiment, the plant or fungi matter is whole plant or fungi matter containing a full spectrum of compounds naturally found in the plant or fungi matter, which is defined as the plant or fungi matter of step 101 having not been subjected to any extraction methods prior to step 101. Next in step 102, the plant or fungi matter is homogenized, such that the matter is blended uniformly. This is an important step to actively determine the compound concentration.

Still referring to FIG. 1, next in step 103, the homogenized plant or fungi matter is tested to determine the compound concentration. Any testing method known in the art may be used, including but not limited to High Performance Liquid Chromatography (HPLC), Thin-Layer Chromatography (TLC), Capillary Electrophoresis (CE), Gas Chromatography (GC), Mass Spectrometry (MS), a combination thereof, or similar. After testing, the particular compound concentration is determined. The end goal of the process is to achieve a desired predetermined dosage (of compound concentration). In one embodiment, microdosing is desired, and most likely after testing, it is determined, the compound concentration is higher than the desired dosage. Thus, in step 104, at least a portion of the compound concentration from the plant or fungi matter is extracted via an extraction method. In some embodiments, the entirety of the compound concentration is extracted. In other embodiments, a portion of the compound concentration is extracted, such as at least 5%. In some embodiments, extracting as much compound concentration as possible is preferred. This will be described in further details below. In other embodiments, regardless of the base level dosage of compound concentration provided in the plant or fungi matter, it may be a particular object of the present invention to add a different compound not naturally found in the matter. Thus, it is desirable to extract as much compound concentration as possible. This will be discussed in further details below.

Any known extracted methods known in the art may be used, including but not limiting to, ultrasonic extraction, centrifugal extraction, CO2 extraction, ice extraction, water extraction, and alcohol extraction. Ultrasonic Extraction is a simple and versatile method for cell disruption and the production of extracts. High-power ultrasound waves are used to isolate targeted compounds from the plant or fungi matter. One main advantage of ultrasound-assisted cell lysis and isolation is the outstanding effectiveness of the extraction procedure, resulting in high yield levels with timely rates of extraction. Additional benefits include a non-thermal process meaning that active compounds are not treated at high temperatures to avoid thermal degradation of the extracts which preserves the extracts' bioactivity. Carbon dioxide supercritical extraction is one application of the supercritical fluid extraction (SFE) process. SFE is a separation technology that uses supercritical fluid solvent for extraction. Carbon dioxide is the most commonly used supercritical fluid, with other choices, including ethanol. Compared with traditional soxhlet extraction, SFE uses supercritical fluid to provide a broad range of useful properties. It eliminates the use of organic solvents, which reduces the problems of their storage, disposal, and environmental concerns. In the extraction process, diffusion coefficients of lipids and waxes in supercritical fluids are much higher than in liquids, therefore extraction can occur more quickly. In addition, no surface tension is present in supercritical fluids, and viscosities are much lower than in liquids, which help the supercritical fluids be able to penetrate into small pores that are inaccessible to liquid. Regarding ice extraction, active compounds like psilocybin or cannabinoids are often removed effectively using cold water or ice. For psilocybin removal, place fresh fungi over ice and leave in a cold temperature environment (above freezing) for a set period of time until the ice it melts into a blue liquid. Next, the fungi are strained away and the blue liquid contains high levels of psychoactive compounds like Psilocybin, Psilocin, baeocystin amongst others. For cannabinoids shaking the *Cannabis* plant matter in a bag with ice (dry ice works best), the cannabinoids separate from the plant matter and can be sifted out. In both cases, freezing liquid or liquid with ice in it also works effectively to separate the desired compounds. Regarding water extraction, the fungi or plant matter is pulverized and soaked in water (hot is preferred), then blended or the use of sonic vibration, or similar motion to help the compounds dissolve into the liquid. Next, the liquid is strained away from the fungi or plant matter. Regarding alcohol extraction, the plant or fungi matter is crushed or pulverized, then dried and placed into alcohol, such as methanol for a predetermined time. The liquid mixture is filtered, and then evaporated as known in the art.

Next in step 105, the plant or fungi matter is homogenized. Next in step 106, additional compounds are added to the plant or fungi matter (of step 101) to reach a desired level of compound concentration within the plant or fungi matter, i.e. the same plant or fungi matter that was provided earlier undergoing the described method. In one embodiment, the additional compounds are any compounds as defined in the list above, for instance obtained from external sources. In some embodiments, the additional compounds are a portion of the extracted compounds of step 103. The desired level is the precision dose that is desired by a user, which may vary for the application or requirements of the user. Next in step 107, the modified plant or fungi matter with the additional compounds is homogenized. Finally, in step 108, the homogenized modified plant or fungi matter with the additional compounds is tested to determine that the desired level is reached. Steps 104-108 may be repeated if necessary if the desired level is not reached.

It should be understood that the method described above may vary, and certain steps may be omitted. For instance, after step 103 (testing) it may be determined that step 104 (extraction) need not be preferred as the level of compound concentration is lower than the desired dose. Alternatively, additional compounds may be added to the naturally provided compound concentration already found in the plant matter or fungi.

It is an object of the present invention to to take the psychedelic compounds from the psychedelic mushroom and adding it to other forms of non-psychedelic mushrooms to add additional benefits and vice-versa. In order to do so, the following method may be performed.

Figure 2:
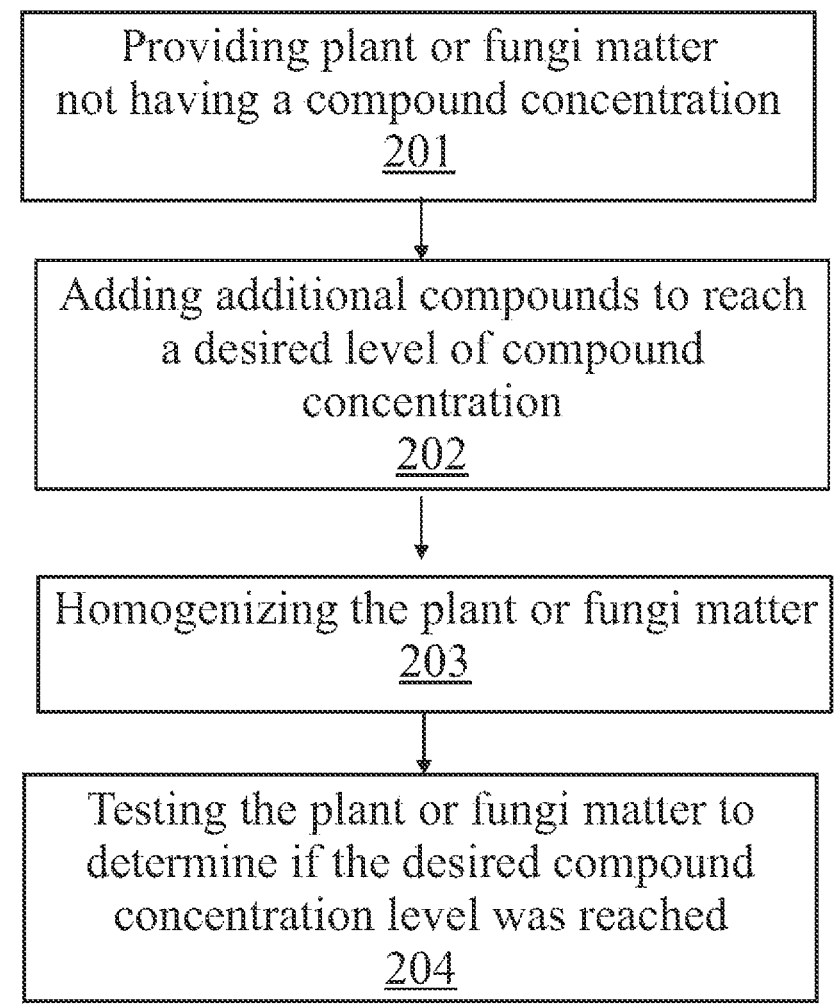
FIG. 2 is a method of precision dosing plant or fungi matter not containing a compound centration according to an embodiment of the present invention.

Now referring to FIG. 2, the method 200 is illustrated. First, in step 201, plant or fungi matter not having a compound concentration is provided, i.e. the plant or fungi matter does not have an active ingredient or compound defined in the previously defined compound definition. It should be understood, that the plant or fungi matter may have a different active ingredient or compound concentration not defined in the list. For example, in the fungi family, Lion's Mane includes active compounds hericenones and erinacines which are configured to aid nerve growth, and is useful to possibly slow Alzheimer's disease. Other fungi, including Turkey Tail, Chaga, Shiitake, Maitake, Reishi, *Cordyceps*, etc. may include active compounds that are not defined in the previously list and for the purposes of this disclosure and claims are considered plant or fungi matter that does not have a compound concentration. Broadly, having a compound concentration includes compounds that have a mind altering effect.

Next in step 202, compounds (as defined) are added to the plant or fungi matter to reach a desired level of compound concentration within the plant or fungi matter. Next in step 203, the plant or fungi matter is homogenized, such that the matter is blended uniformly. Last, in step 204, the homogenized modified plant or fungi matter with the added compounds is tested to determine that the desired level is reached. In some embodiments, a homogenized step may also be performed after step 201.

Although the fungi example was provided for method 200, it should not be construed as limiting. For example, in another embodiment, using method 200, a user can add cannabinoids such as, but not limited to, CBD or THC to fungi such as Lion's Mane, other fungi, or plant matter.

It's an object of the present invention to provide a cross-over of compounds from one species or strain of one plant matter or fungi into another, wherein the strains may be combined or kept separate. The following method steps below provide a non-limiting example.

Figure 3A:
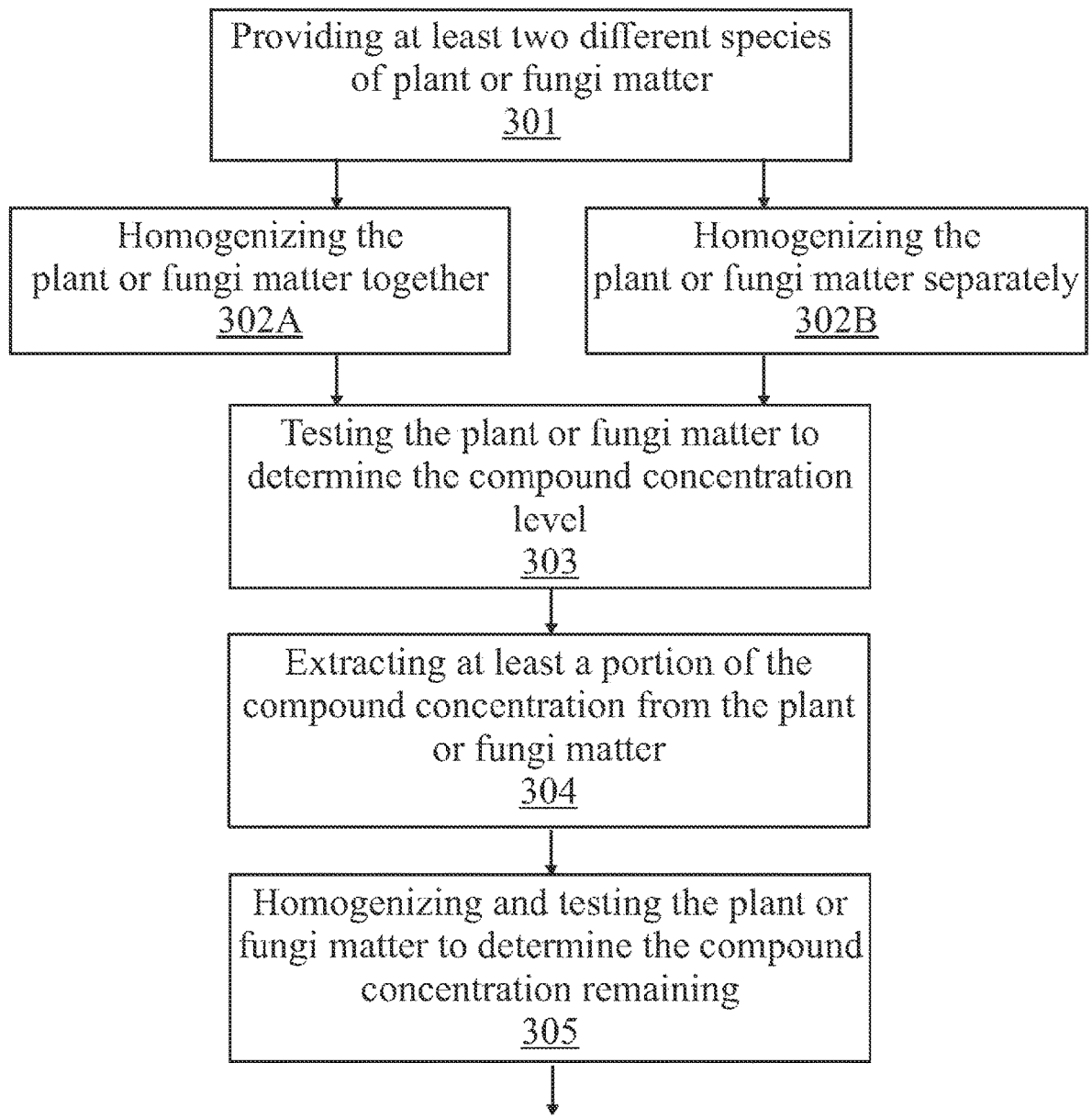
FIGS. 3A-B show a method of precision dosing at least two plant or fungi matters according to an embodiment of the present invention.
Figure 3B:
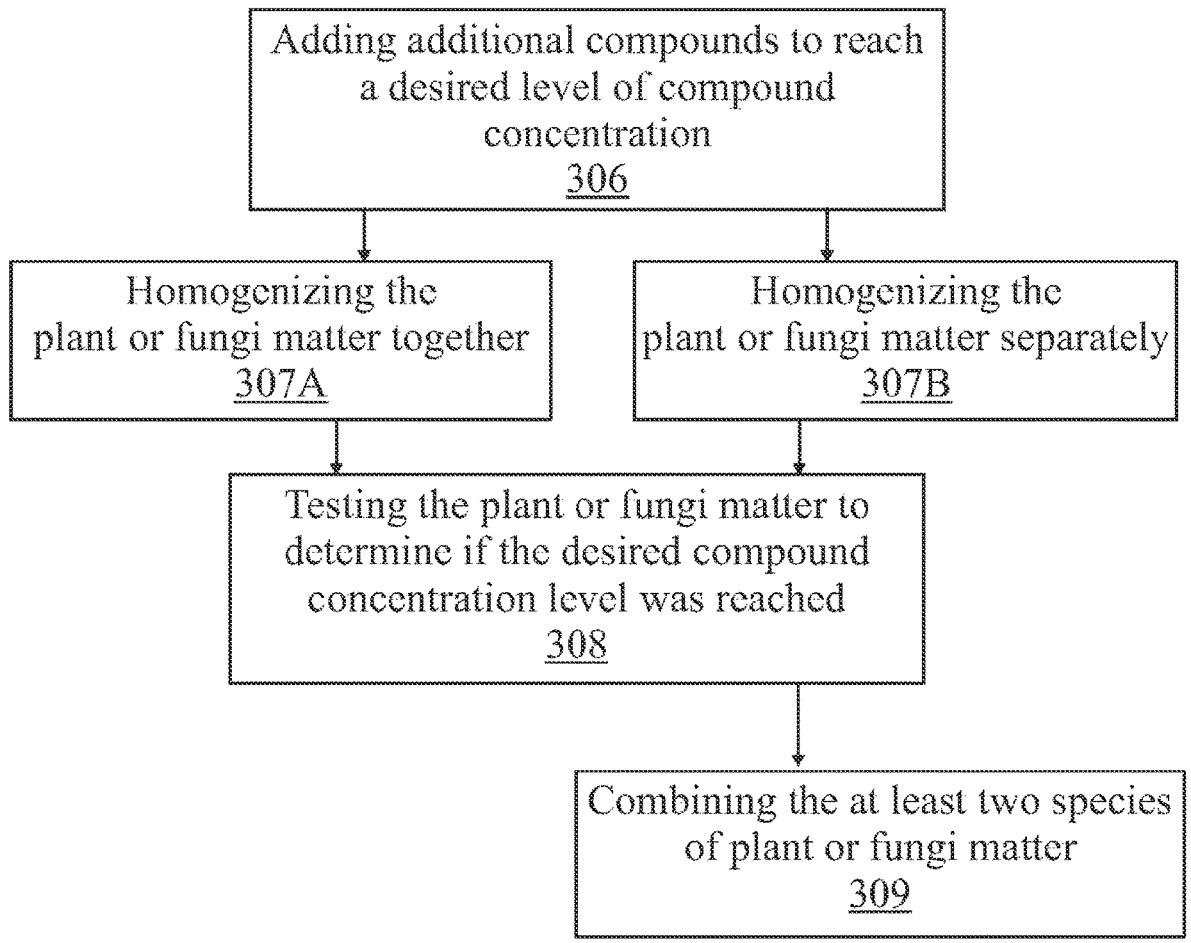

Now referring to FIGS. 3A-B, the method 300 includes a first step 301 of providing plant or fungi matter of at two different species or strains. The first plant matter or fungi matter has a compound concentration as previously defined. The second plant matter or fungi matter may have or not have a compound concentration as previously defined. It should be understood, that more than two different species or stains may be provided, wherein at least one of the provided species or strains of plant or fungi matter should contain a compound concentration as previously defined. This may include plant or fungi matter in the same family or not. For example, two or more different species of psychedelic mushrooms, or a *Cannabis* species and a psychedelic mushroom.

Next in step 302A, the first and second plant or fungi matters are homogenized together to form a blend. Alternatively, in step 302B, the first and second plant or fungi matters are each homogenized separately. Next in step 303, the first and second homogenized plant or fungi matter is tested to determine the compound concentration, wherein the first and second homogenized plant or fungi matter are tested in a blended state or tested separately based on the respective method steps. Next in step 304, optionally (if needed or desired), an extraction method is performed to the first and/or second plant or fungi matter to remove at least a portion of the compound concentration from the first and/or second plant or fungi matter. Next in step 305, if step 304 is carried out, the extracted matter is homogenized and tested again to determine the concentration of compounds remaining. Next, in step 306, additional compounds at a predetermined concentration are added to the blended or separated first and second plant or fungi matter such that a desired level is reached. It should be noted, that the compounds may be any compounds previously defined, and may include compounds not naturally found in the plant or fungi matter. Next, in step 307A, the first and second plant or fungi matter with the added compounds are homogenized together. Alternatively, in step 307B, the first and second plant or fungi matter with the added compounds are homogenized separately. Next in step 308, the first and second homogenized plant or fungi matter is tested to determine the compound concentration after the additional compounds were added. Last, optionally, in step 309 if not already done so, the first and second homogenized plant or fungi matter may be combined, blended, or homogenized, wherein the combination may include a portion of each such that a desired concentration of compounds is reached. Testing may be repeated to see if the desired concentration of compounds was reached. Steps may be repeated if necessary to achieve desired results.

The plant or fungi matter of the present invention may be in any form, including its natural form, a solid form, a liquid form, or powder form. After the various methods have been performed, the resulting matter with the precision dosage may be delivered or provided to the user in a variety of methods, including but not limited to pill form, natural form, tinctures, beverages, or with the use of delivery devices such as coffee or tea machines. For example, in one embodiment, the precision dosed plant or fungi matter may be positioned in a single use coffee delivery pod, below, above, or outside the coffee filter such that the precision dosed plant or fungi matter enters the user's coffee during the brewing process. In other embodiments, the plant or fungi matter not having a compound concentration may be placed below, above, or outside the coffee filter. In some embodiments, the plant or fungi matter not having a compound concentration may be reduced to a Nano-powder to improve the delivery and absorption properties, wherein the Nano-powder contains particles, and at least 5% of the particles are smaller than 1000 Nanometers. Likewise, the precision dosed plant or fungi matter may be reduced to a Nano-powder to improve the delivery and absorption properties. In one embodiment, in the Nano-powder contains particles, wherein at least 5% of the particles are smaller than 1000 Nanometers. In yet other embodiments, compounds as previously defined, may be placed below, above, or outside the coffee filter. In some embodiments, these compounds were previously extracted as described above, or are additional compounds provided by another source.

In alternative embodiments, compounds may be infused or added to plant or fungi matter that have a level of compound concentration (active compounds) without previously extracting a portion of these compounds before the compounds are added. For example, (a) providing plant or fungi matter having a compound concentration; (b) optionally testing the plant or fungi matter to determine the compound concentration level; and (c) adding additional compounds to the plant or fungi matter to reach a desired level of compound concentration within the plant or fungi matter.

In alternative embodiments, the matter may include fruit, vegetable, meat, poultry, fish, nut, and spices. The matter may be in any state (solid, liquid, or gas), and which is subjected to method 200. That is compounds are added to the matter to reach a desired level of compound concentration. The matter and compounds may be homogenized and tested to ensure the desired compound concentration level was reached. Advantageously, this allows matter with non-active compounds, including but not limited to cannabinoids, psychedelics, ketamine, MDMA, etc. to be infused in matter such as fruit, vegetable, meat, poultry, fish, and spices. For example, orange juice infused with cannabinoids, almond milk infused with psychedelics, vegetable powder infused with LSD, black pepper infused with CBD, or poultry infused with MDMA. As previously mentioned, the matter may be in any state and also any consistency and particle size, such a powder form, natural form, liquid, oil, etc.

Although the invention has been described in considerable detail in language specific to structural features and or method acts, it is to be understood that the invention defined in the appended claims is not necessarily limited to the specific features or acts described. Rather, the specific features and acts are disclosed as exemplary preferred forms of implementing the claimed invention. Stated otherwise, it is to be understood that the phraseology and terminology employed herein, as well as the abstract, are for the purpose of description and should not be regarded as limiting. Therefore, while exemplary illustrative embodiments of the invention have been described, numerous variations and alternative embodiments will occur to those skilled in the art. Such variations and alternative embodiments are contemplated, and can be made without departing from the spirit and scope of the invention.

In addition, references to "first," "second," "third," and etc. members throughout the disclosure (and in particular, claims) are not used to show a serial or numerical limitation but instead are used to distinguish or identify the various members of the group.

What is claimed is:

1. A method of precision compound concentration dosing for fungi comprising steps:
    (a) providing fungi matter having a concentration of one or more psychedelic compounds;
    (b) extracting at least a portion of the concentration of the one or more psychedelic compounds from the fungi matter via an extraction method; and,
    (c) adding additional psychedelic compounds to the remaining fungi matter from step (b) to achieve a desired concentration level of the one or more psychedelic compounds within the fungi matter.

2. The method of precision compound concentration dosing for fungi of claim 1, wherein the fungi matter is homogenized after step (a), (b), or (c).

3. The method of precision compound concentration dosing for fungi of claim 1, further comprising a step of testing the fungi matter to determine the concentration of the one or more psychedelic compounds after steps (a), (b), or (c).

4. The method of precision compound concentration dosing for fungi of claim 1, wherein step (b), the extraction method is an extraction method selected from a liquid extraction, a chemical extraction, or a mechanical extraction.

5. The method of precision compound concentration dosing for fungi of claim 1, wherein step (a), the fungi matter is in its natural form, a liquid form, a solid form, or powder form.

6. A method of precision compound concentration dosing for fungi comprising steps:
    (a) providing fungi matter having a concentration of one or more psychedelic compounds;
    (b) extracting at least a portion of the concentration of the one or more psychedelic compounds from the fungi matter via an extraction method;
    (c) testing the fungi matter to determine the remaining concentration of the one or more psychedelics compounds; and,
    (d) adding additional psychedelic compounds to the remaining fungi matter from step (c) to achieve a desired concentration level of the one or more psychedelic compounds within the fungi matter.

7. The method of precision compound concentration dosing for fungi of claim 6, further comprising a step (e), testing and analyzing the fungi matter to determine if the desired concentration level of the one ore more psychedelic compounds was achieved.

8. The method of precision compound concentration dosing for fungi of claim 6, further comprising a step of testing the fungi matter to determine the concentration of the one or more psychedelic compounds prior to step (b).

9. The method of precision compound concentration dosing for fungi of claim 6, wherein the fungi matter is homogenized after step (a), (b), and (d).

10. The method of precision compound concentration dosing for fungi of claim 6, wherein step (a), the fungi matter is in its natural form, a liquid form, a solid form, or a powder form.

11. The method of precision compound concentration dosing for fungi of claim 6, further comprising a step of providing additional fungi matter not having a concentration of psychedelic compounds, wherein the additional fungi matter is homogenized with the fungi matter.

* * * * *